(12) United States Patent
Rustici et al.

(10) Patent No.: US 9,301,914 B1
(45) Date of Patent: Apr. 5, 2016

(54) BODY COSMETIC FOR WETTED SKIN

(71) Applicant: Kao USA Inc., Cincinnati, OH (US)

(72) Inventors: Jessica Rustici, Covington, KY (US); Alisa Smith, Cincinnati, OH (US); Paula Thueneman, Taylor Mill, KY (US)

(73) Assignee: Kao USA, Inc., Cincinnati, OH (US)

( * ) Notice: Subject to any disclaimer, the term of this patent is extended or adjusted under 35 U.S.C. 154(b) by 0 days.

(21) Appl. No.: 14/736,588

(22) Filed: Jun. 11, 2015

(51) Int. Cl.
| | |
|---|---|
| *A61Q 19/10* | (2006.01) |
| *A61K 8/90* | (2006.01) |
| *A61K 8/06* | (2006.01) |
| *A61K 8/37* | (2006.01) |
| *A61K 8/31* | (2006.01) |
| *A61K 8/34* | (2006.01) |
| *A61Q 19/00* | (2006.01) |

(52) U.S. Cl.
CPC ... *A61K 8/90* (2013.01); *A61K 8/31* (2013.01); *A61K 8/345* (2013.01); *A61K 8/37* (2013.01); *A61Q 19/007* (2013.01)

(58) Field of Classification Search
None
See application file for complete search history.

(56) References Cited

U.S. PATENT DOCUMENTS

| | | |
|---|---|---|
| 5,004,598 A | 4/1991 | Lochhead et al. |
| 5,221,534 A | 6/1993 | DesLauriers et al. |
| 5,928,632 A | 7/1999 | Reusch |
| 2008/0085961 A1* | 4/2008 | Lin .................. A01N 25/04 524/313 |

FOREIGN PATENT DOCUMENTS

| | | |
|---|---|---|
| JP | 2004-231518 A | 8/2004 |
| JP | JP 2005-526118 A | 9/2005 |

* cited by examiner

*Primary Examiner* — H. Sarah Park
(74) *Attorney, Agent, or Firm* — Frost Brown Todd LLC

(57) ABSTRACT

A body cosmetic for application to wetted skin after showering, and the like, which provide high moisturizing effects, all over body spreadability, and easy application with a non-greasy and non-sticky feeling. An oil-in-water body cosmetic for application to wetted skin, which contains the following components (A) to (D): (A) from about 0.1% to about 1% of block copolymer; (B) from about 3% to about 10% branched fatty acid ester; (C) from about 3% to about 20% hydrocarbon oil; and (D) from about 5% to about 50% glycerin.

10 Claims, No Drawings

BODY COSMETIC FOR WETTED SKIN

FIELD OF THE INVENTION

The present invention relates to body cosmetics for application to wetted skin and a skin care method using the same.

BACKGROUND

Conventionally, a variety of skin care cosmetics intended for the face, hands, and the like have been widely used to prevent skin dryness or roughness. In recent years, however, skin care cosmetics for the whole body have been used, because skin dryness, roughness, or other skin conditions occur not only on the face but also on parts of a body such as hands, arms, and legs. Such skin care cosmetics are required to have non-stickiness, non-greasiness and ease of application to the whole body, in addition to excellent moisturizing effects. Usually, as skin care agents or skin conditioners for use after bathing or for use in a daily skin care routine, body lotions or milks on dry skin and the like are used. And for use in bathing, shower agents and the like are used. From this point of view, body rinse compositions used by applying to wetted skin after bathing and lightly rinsing off (U.S. Pat. No. 5,928,632), rinsable skin conditioning compositions (JP-A-2005-526118), shower agents (JP-A-2004-231518), and the like have been developed.

SUMMARY

The present invention provides an oil-in-water body cosmetic for application to wetted skin, which contains the following components (A) to (D):

(A) from about 0.1% to about 1.5% of at least one block copolymer chosen from diblock copolymers, triblock copolymers, multiblock copolymers, and radial block copolymers, wherein said at least one block copolymer comprises at least one segment derived from at least one thermoplastic entity chosen from thermoplastic monomers and thermoplastic comonomers;

(B) from about 3% to about 10% branched fatty acid ester;

(C) from about 3% to about 20% hydrocarbon oil; and (D) from about 5% to 50% glycerin.

Further provided by the invention is a cosmetic method for application to wetted skin of a composition of the invention.

DETAILED DESCRIPTION

The above-described prior art conventional cosmetics for the whole body are used by applying to wetted skin and then rinsing off in a shower or the like, and hence were difficult to provide sufficient skin care benefits because of low retention of moisturizers, i.e., active ingredients. Moreover, increasing the retention of moisturizers problematically caused a sticky feeling, left a greasy residue, and caused spreading on skin to deteriorate, making the application unpleasant.

In contrast, the present invention provides body cosmetics for application to wetted skin after showering or the like, having high moisturizing effects, all over body spreadability, and easy application with a non-greasy and non-sticky feeling.

Thus, the present inventors paid attention to an oil-in-water emulsion containing a block copolymer. And they added a certain amount of branched fatty acid ester and hydrocarbon oil in combination into the emulsion as oily ingredients, and further added a large amount of glycerin thereto. In addition, an amount of non-soluble powder may be added to the composition. As a result, the emulsion spreads extremely well when applied to wetted skin, and provides enhanced and long-lasting moisturizing effects. Moreover, the inventors found that the oil-in-water cosmetics of the invention preferably are not rinsed off after application to wetted skin, and after drying, the cosmetics can provide excellent, long lasting skin care benefits.

The body cosmetics of the present invention spread extremely well when applied directly to wetted skin, and provide good moisturizing effects after application, such as a moist feeling, and a smooth feeling, which last for a long time. In addition, the body cosmetics can show the above-described excellent effects simply by applying to wetted skin and then towel drying; hence, they can provide these effects only by a simple process after bathing. In addition, the formula does not leave a greasy residue.

The body cosmetics for wetted skin of the present invention are in the form of oil-in-water emulsions wherein oily ingredients are dispersed along optimally with a water insoluble powder in an aqueous phase containing glycerin.

Content of the block copolymer in the body cosmetics of the invention is preferably from about 0.1% to about 1.5% by mass (hereinafter simply denoted as %), and more preferably from about 0.3% to about 0.7%, to provide stability, ease of application, and moisturizing effects to the oil-in water emulsions.

The block copolymers which can be used according to the present invention include, for example, those disclosed in U.S. Pat. No. 5,221,534 DesLauriers et al., issued Jun. 22, 1993, the disclosure of which is incorporated herein by reference. In general, the compositions of the present invention contain about 80% to about 99% of an oil, and about 1% to about 20% of copolymer which includes at least one or either a di-block or tri-block polymer which consist of a hard segment, such as butadiene. Tri-block copolymers of styrene/ethylene/propylene or di-block copolymers of styrene/ethylene/propylene and styrene/butylene/ethylene are employed to gel the oil. Such block copolymers are available under the Versagel® series from Penreco.

Preferred within the context of the present invention is gelled mineral oil containing block polymers having the INCI name "Mineral Oil and Ethylene/Propylene/Styrene Copolymer and Butylene/Ethylene/Styrene Copolymer". Representatives thereof are available, for example, under the trade names Versagel® M200 and Versagel® M750 (Penreco).

The invention importantly includes a branched fatty acid ester, in addition to the block copolymer, such as the gelled mineral oil.

Examples of the branched fatty acid ester include ethylhexyl isononanoate, isotridecyl isononanoate, octyldodecyl myristate, octyldodecyl oleate, cetyl 2-ethylhexanoate, isocetyl 2-ethylhexanoate, and isostearyl isostearate; oxyacid esters of a higher alcohol such as diisostearyl malate and cetyl lactate; and fatty acid esters of a polyol such as propylene glycol diisostearate, glyceryl tricaprylate, glyceryl tri-2-ethylhexanoate, glyceryl triisostearate, glyceryl (tricaprylate•caprate), propylene glycol dicaprylate, propylene glycol di(caprylate•caprate), propylene glycol diisostearate, neopentyl glycol dicaprate, and neopentyl glycol 2-ethylhexanoate; and combinations of those materials.

The content of these branched fatty acid ester in the body cosmetics of the invention is preferably from about 3% to about 10%, more preferably from about 4% to about 9%, and still more preferably from about 5% to about 8%.

The body cosmetic of the invention preferably further contains water-insoluble or almost insoluble powders to improve the skin feeling upon application, such as a silky feeling, non-greasy, and a smooth feeling.

Examples of water-insoluble powders include inorganic powders such as talc, sericite, kaolin, clay, swellable clays, silicic acid, silicic acid anhydride, magnesium aluminum silicate, magnesium silicate, mica isinglass, magnesium oxide, aluminum oxide, aluminum sulfate, alum, calcium sulfate, and barium sulfate; organic powders such as polyamide, polyester, polyethylene, polypropylene, polystyrene, ethylene-acrylic acid polymer, styrene-acrylic acid copolymer, polyurethane, vinyl resin, polycarbonate resin, nylon, silk, cellulose powder, silicone powder, and polyacrylic acid. Among these examples, talc, kaolin, magnesium aluminum silicate, and silicone powder are preferable in the body cosmetics of the invention because they can provide a good feeling on skin. In addition, starches such as aluminum starch octenylsuccinate and corn starch can be used.

These powder particles may have any of flat, mass, scaly, spherical and like shapes. These water-insoluble powders preferably have a mean particle size of from about 0.1 to about 100 μm, more preferably from about 1 to about 50 μm, and most preferably from about 1 to about 10 μm.

The content of these water-insoluble powders in the body cosmetics of the invention is preferably from about 0.01% to about 5%, and more preferably from about 0.1% to about 1%, to improve the feeling at the time of application.

It is important that the body cosmetics of the invention contain from about 5% to about 50% of glycerin to provide a moist feeling on skin after application to wetted skin and excellent moisturizing effects. The content of glycerin is more preferably from about 15% to about 45%, and still more preferably from about 20% to about 35%. Since a large amount of glycerin is contained therein, the body cosmetics of the invention provide notably excellent moisturizing effects when applied to skin.

Since the body cosmetics of the invention are used by directly applying to wetted skin, they preferably contain the oily ingredients and glycerin in a total amount of about 80% or less, and more preferably from about 30% to about 70%, to provide wet spreadability and non-stickiness at the time of application to wetted skin, as well as a moist feeling and non-stickiness after towel drying.

The body cosmetics of the invention contain water in an amount of from about 20% to about 80%, preferably from about 30% to about 70%, and still more preferably from about 40% to about 60%, from a viewpoint of stability.

The body cosmetic of the invention optimally also contains from about 3% to about 20% hydrocarbon oil that forms the basis for the oil-in-water emulsion. More preferably the hydrocarbon oil content is from about 5% to about 15% and still more preferably from about 10% to about 15%.

Non-limiting examples of suitable non-polar hydrocarbon oils include mineral oils and branched chain hydrocarbons (such as commercially available, for example, under the trade names Permethyl™ (Permethyl Corporation™) and Isopar™ (Exxon™)).

The oil-in-water composition importantly contains an emulsion stabilizer such as a cross-linked acrylic acid or a modified copolymer such as that disclosed in U.S. Pat. No. 5,004,598, Lochhead et al., issued Apr. 2, 1991, the disclosure of which is incorporated herein by reference. Carbopol polymers available from Lubrizol such as ETD2020 are preferred.

The amount of emulsion stabilizer is the body composition is from about 0.01% to about 5%, and preferably from about 0.1% to about 1%.

In the present invention, it is important that the amount of fatty acid ester and the amount of hydrocarbon should be contained in the oil phase to achieve both excellent moisturizing effects and a spreading effect of the oily ingredients on wetted skin. In order to achieve these effects, the mass ratio of the fatty acid ester and the hydrocarbon oil to glycerin is preferably from about 1:10 to about 5:1, more preferably from about 1:5 to about 5:1, and still more preferably from about 1:5 to about 2:1.

In addition to the above-described ingredients, the body cosmetics of the invention may contain various medicinal components, anti-inflammatory agents, UV blocking agents, botanical extracts, skin conditioning agents, skin enhancing agents, antimicrobial agents, antiperspirants, preservatives, antioxidants, pigments, perfumes, and the like. Insofar as the effects of the invention are not impaired, the body cosmetics may further contain a small amount of surfactants, preferably in an amount of about 1% or less and more preferably about 0.5% or less.

Non-limiting examples of additional skin enhancing agents include *Theobromo Cacao* Extract; *Camellia Sinensis* Leaf Extract; *Fragaria Vesca* (Strawberry) Fruit Extract; *Zingiber Officinale* Leaf Extract; *Prunus Domestica* Fruit; *Punic Granatum* Leaf Extract; *Helianthus Annuus* (Sunflower) Seed Extract; *Citrus Medica Limonum* (Lemon) Peel Extract; *Chamomilla Recutita* (Matricaria) Flower Extract; *Helianthus Annuus* (Sunflower) Seed Oil; *Triticum Vulgare* (Wheat) Germ Oil; *Tritium Vulgare* (Wheat) Germ Extract; *Citrus Medica Limonum* (Lemon) Peel Extract; Coconut Oil; *Helianthus Annuus* (Sunflower) Seed Oil; Argan Oil; *Gardenia Tahitensis* Extract; and combinations thereof.

The composition optionally may further include ingredients that help maintain the integrity of the emulsion, such and antioxidants, chelating agents, and preservatives. Materials suitable for use in cosmetic formulations are well known to those skilled in the art. Illustrative examples of preservatives include, chlorhexidine, ethylparaben, propylparaben methylparaben, EDTA or salts thereof (such as disodium EDTA), phenoxyethanol, DMDM hydantoin, and the like, or combinations thereof. The preservative may be present in any effective amount, such as an amount of from about 0.01% to about 3% by weight of the composition.

Since the body cosmetics of the invention are in a form of oil-in-water emulsions wherein oily ingredients are dispersed in an aqueous phase containing a water-soluble polymer, these emulsions can be stably blended with a large amount of glycerin, and can also provide the effects of the invention, as described above. In order to produce such stable emulsions, the oily phase/aqueous phase mass ratio is preferably from about 10/90 to about 50/50 and more preferably from about 15/85 to about 40/60.

The body cosmetics of the invention preferably have a viscosity of from about 1,000 to about 100,000 mPas, more preferably from about 10,000 to about 50,000 mPas, and still more preferably from about 15,000 to about 30,000, to achieve stability of the oil-in-water emulsions. The measurement conditions are as follows; equipment used: Brookfield viscometer with T-C spindle and heliopath; rotation speed: 10 r/min; measurement time: 60 sec; measurement temperature: 25° C.

The body cosmetics of the invention are used by applying to wetted skin after bathing, showering, or the like. From about 5 g to about 15 g are applied per application. When applied to wetted skin, the body cosmetics spread well to the skin, and release the oil-in-water emulsions, which then are attached to the skin surface. At that time hydrocarbon oil and glycerin are also uniformly attached all over the skin, such that the ingredients synergistically provide high moisturizing effects and a smooth feeling which last for a long time. After application, the body cosmetics of the invention may be rinsed off in a shower, however, it is more preferred to apply without rinsing and therefore drying as usual.

EXAMPLES

The following examples are provided to further illustrate the invention. These examples are illustrative only and are not intended to limit the scope of the invention in any way.

Example 1

|  |  | % |
|---|---|---|
| Oil Phase | Mineral Oil | 4.75 |
|  | Versagel M200 | 10.00 |
|  | Ethylhexyl Isononanoate | 8.00 |
| Water Phase | Deionized Water | 58.00 |
|  | Glycerin USP | 17.00 |
|  | ETD2020 | 0.25 |
|  | Ceteareth-20 | 0.50 |
|  | Talc | 0.85 |
|  | Methylparaben | 0.10 |
|  | Ethylparaben | 0.10 |
|  | DMDM Hydantoin | 0.20 |
|  | Argan Oil | 0.25 |

Example 2

|  |  | % |
|---|---|---|
| Oil Phase | Mineral Oil | 20.50 |
|  | Ethylene/Propylene/Styrene Copolymer (and) Butylene/Ethylene/Styrene Copolymer | 0.10 |
|  | Ethylhexyl Isononanoate | 3.60 |
| Water Phase | Deionized Water | 49.10 |
|  | Glycerin USP | 25.65 |
|  | Acrylates/C10-30 Alkyl Acrylate Crosspolymer | 1.00 |
|  | Ceteareth-20 | 0.10 |
|  | Magnesium Aluminum Silicate | 0.05 |
|  | Phenoxyethanol | 0.40 |
|  | Cocoa Butter | 0.05 |

Example 3

|  |  | % |
|---|---|---|
| Oil Phase | Mineral Oil | 5.50 |
|  | Ethylene/Propylene/Styrene Copolymer (and) Butylene/Ethylene/Styrene Copolymer | 1.00 |
|  | Ethylhexyl Isononanoate | 4.00 |
| Water Phase | Deionized Water | 59.40 |
|  | Glycerin USP | 27.50 |
|  | Acrylates/C10-30 Alkyl Acrylate Crosspolymer | 0.40 |
|  | Ceteareth-20 | 0.10 |
|  | Silicone powder | 0.55 |

-continued

|  | % |
|---|---|
| Salicylic Acid | 0.10 |
| Aloe Vera Extract | 1.00 |

What is claimed is:

1. An oil-in-water skin conditioning composition comprising:
    (A) from about 0.1% to about 1.5% of at least one block copolymer chosen from diblock copolymers, triblock copolymers, multiblock copolymers, and radial block copolymers, wherein said at least block copolymer comprises at least one segment derived from at least one thermoplastic entity chosen from thermoplastic monomers and thermoplastic comonomers;
    (B) from about 3% to about 10% branches fatty acid ester;
    (C) from about 3% to about 20% hydrocarbon oil; and
    (D) from about 5% to about 50% glycerin.

2. The composition according to claim 1 wherein the ratio of the ingredient (B) and ingredient (C) to ingredient (D) is from about 1:10 to about 5:1.

3. The composition according to claim 1 wherein said composition further comprises from about 0.01% to about 5% water-insoluble powder.

4. The composition according to claim 1 wherein said composition further comprises from about 20% to about 80% water.

5. The composition according to claim 1, wherein the hydrocarbon oil is selected from mineral oil, petrolatum, and mixtures thereof.

6. The composition according to claim 1 wherein the block copolymer is a di-block copolymer, a tri-block copolymer, or a mixture thereof.

7. The composition according to claim 6 wherein the block copolymer is selected from the group consisting of ethylene/propylene/styrene copolymers, butylene/ethylene/styrene copolymer, and mixtures thereof.

8. A method comprising applying an oil-in-water body cosmetic for wetted skin to skin wetted with water and then drying the skin wherein the body cosmetic comprises the following components:
    (A) from about 0.1% to about 1% of at least one block copolymer chosen from diblock copolymers, triblock copolymers, multiblock copolymers, and radial block copolymers, wherein said at least one block copolymer comprises at least one segment derived from at least one thermoplastic entity chosen from thermoplastic monomers and thermoplastic comonomers;
    (B) from about 3% to about 10% branches fatty acid ester;
    (C) from about 3% to about 20% hydrocarbon oil; and
    (D) from about 5% to about 50% glycerin.

9. The method according to claim 8 wherein the ratio of the ingredient (B) and ingredient (C) to ingredient (D) is from about 1:10 to about 5:1.

10. The method according to 8 wherein the wetted skin is not rinsed after application of the composition.

* * * * *